United States Patent [19]
Nomura et al.

[11] Patent Number: 6,096,372
[45] Date of Patent: Aug. 1, 2000

[54] METHOD FOR MANUFACTURING $O_2$ SENSOR WITH SOLID ELECTROLYTE MEMBER USING CONDUCTIVE PASTE ELEMENT

[75] Inventors: Satoru Nomura, Nisshin; Yasumichi Hotta, Mie-gun; Namitsugu Fujii, Yokkaichi; Hiromi Sano, Nagoya, all of Japan

[73] Assignee: Denso Corporation, Kariya, Japan

[21] Appl. No.: 09/010,839

[22] Filed: Jan. 22, 1998

[51] Int. Cl.[7] .................................................. B05D 5/12
[52] U.S. Cl. ........................... 427/123; 427/231; 427/238
[58] Field of Search .................................. 204/428, 429; 427/123, 125, 231, 238

[56] References Cited

U.S. PATENT DOCUMENTS

| | | | |
|---|---|---|---|
| 4,264,647 | 4/1981 | Trevorrow . | |
| 5,522,979 | 6/1996 | Tatumoto et al. | 427/125 |
| 5,948,225 | 9/1999 | Katafuchi et al. | 427/125 |

FOREIGN PATENT DOCUMENTS

| | | |
|---|---|---|
| 52-94195 | 8/1977 | Japan . |
| 57-182158 | 11/1982 | Japan . |
| 9-72876 | 3/1997 | Japan . |
| 9-145669 | 6/1997 | Japan . |

*Primary Examiner*—Brian K. Talbot
*Attorney, Agent, or Firm*—Pillsbury Madison & Sutro LLP

[57] ABSTRACT

In a method for forming an inside electrode within a cup-type electrolyte member of an $O_2$ sensor element, firstly, a nozzle having a paste discharge hole is prepared. The nozzle is inserted into an inside space of the electrolyte member. Then, the paste discharge hole of the nozzle is relatively rotated with respect to the electrolyte member along an inside surface of the electrolyte member while discharging paste therefrom onto the inside surface. Accordingly, the inside electrode formation portion is formed. After forming the inside electrode formation portion, the electrolyte member is baked. As a result, the inside electrode can be disposed on a required portion of the electrolyte member with a uniform thickness.

24 Claims, 8 Drawing Sheets

FIG. 8A
FIG. 8B
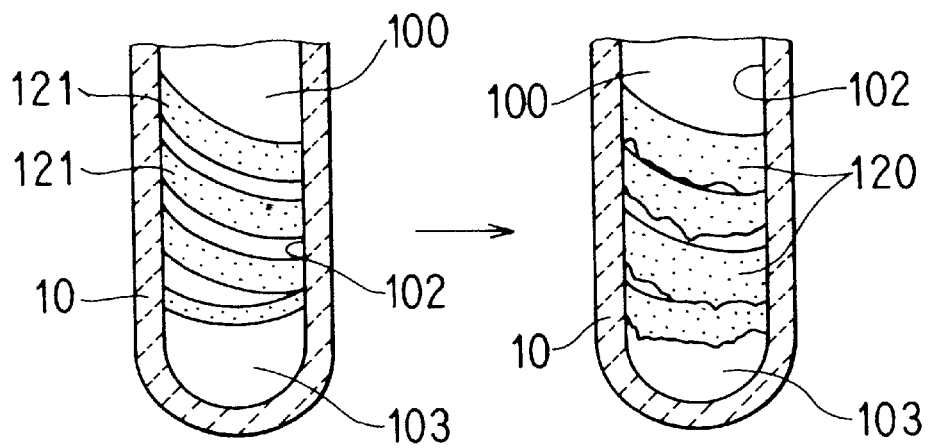
FIG. 9
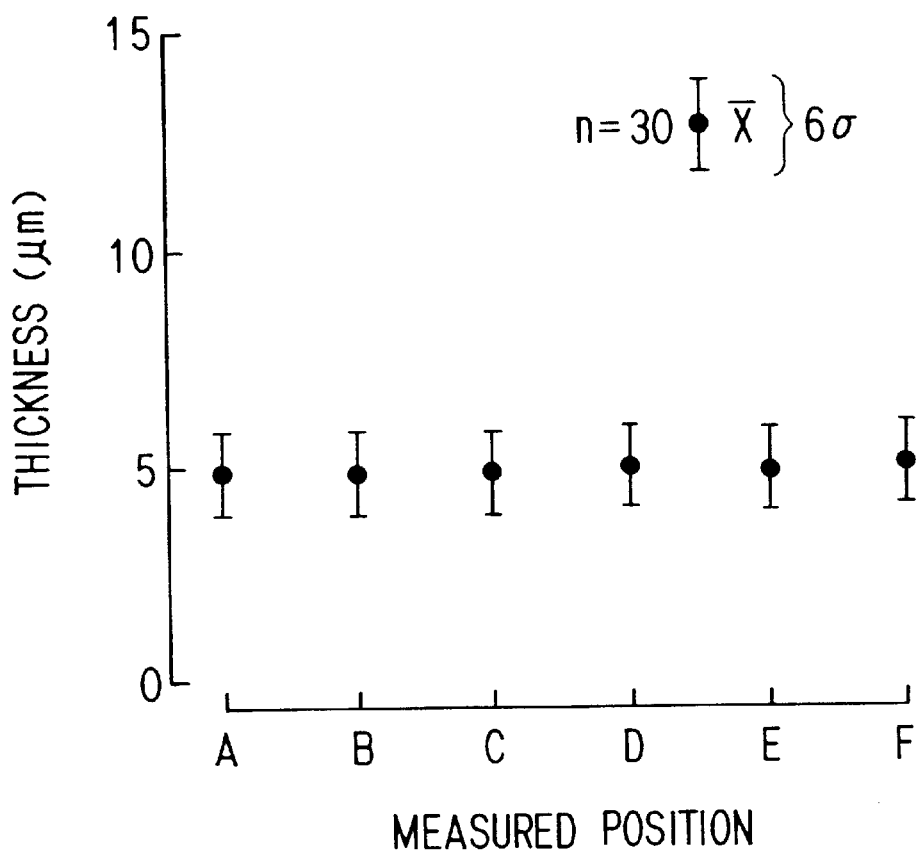

METHOD FOR MANUFACTURING $O_2$ SENSOR WITH SOLID ELECTROLYTE MEMBER USING CONDUCTIVE PASTE ELEMENT

CROSS REFERENCE TO RELATED APPLICATION

This application is based upon and claims the benefit of priority of the prior Japanese Patent Application No. 9-26034 filed on Jan. 23, 1997, the contents of which are incorporated herein by reference.

BACKGROUND OF THE INVENTION

1. Field of the Invention

The present invention relates to a method and an apparatus for manufacturing an $O_2$ sensor element that is generally used for controlling an air fuel ratio of an internal combustion engine for a vehicle.

2. Related Arts

Conventionally, $O_2$ sensor elements of oxygen concentration electromotive force type using zirconium oxide ($ZrO_2$) solid electrolyte and of limit current type are well-known as gas detectors for detecting an oxygen concentration in an exhaust gas from an internal combustion engine of a vehicle. These kinds of $O_2$ sensor elements have been already commercialized.

A typical one of the $O_2$ sensor elements is shown in FIG. 1. The $O_2$ sensor element 9 has a cup-type solid electrolyte member 10 including an inside space 100 therein having an opening at an end thereof. The solid electrolyte member 10 further has an outside electrode 11 on an outside surface 101 thereof, and an inside electrode 94 on an inside surface 102 thereof within the inside space 100. The inside electrode 94 is composed of a reaction electrode 92 and a lead portion 93. The thus designed $O_2$ sensor element 9 is the current mainstream because it is suitable for mass production. Further, a heater 19 is widely adopted to the $O_2$ sensor element 9 to be held in the inside space 100 of the solid electrolyte member 10 as shown in FIG. 1, thereby obtaining sufficient operational properties at a low temperature and high flexibility of an installed position to the vehicle.

However, the $O_2$ sensor element 9 has the following problems. That is, a temperature of the solid electrolyte member 10 around a tip portion thereof becomes high by being exposed to the exhaust gas, however, the temperature of the electrolyte member 10 is lowered as it becomes close to the opening thereof. Because of this, in a case where the reaction electrode 92 is formed on the entire inside surface of the electrolyte member 10 in which the heater 9 is no held, output properties of the reaction electrode 92 deteriorate due to the temperature distribution thereof. Further, even if the heater 19 is held within the $O_2$ sensor element 9, there arises temperature distribution of the reaction electrode 92 due to a heating portion 190 of the heater 9, and the sensor properties are adversely affected by the temperature distribution.

Therefore, in the $O_2$ sensor element 9 without holding the heater 19 therein, the reaction electrode 92 is disposed only around the tip portion of the electrolyte member 10. Further, in the $O_2$ sensor element 9 holding the heater 19 therein, the reaction electrode 92 is disposed only on a specific portion of the electrolyte member 10 facing the heating portion 190 of the heater 19. Accordingly, sensor properties can be improved. In addition, in these cases, the area of the reaction electrode 92 is decreased, so that an amount of material for the reaction electrode 92 is reduced. The reaction electrode 92 usually includes noble metal such as platinum (Pt). Therefore, decrease of the area of the reaction electrode 92 means decrease of material cost.

Conventionally, as a method for manufacturing the above-mentioned $O_2$ sensor element 9, the following method is well-known. That is, firstly, a provisionally baked or finally baked cup-type solid electrolyte member 10 having an inside space 100 is prepared. Then, a jig for coating a paste for an inside electrode is inserted into the inside space 100 of the solid electrolyte member 10. The jig has a hollow pipe formed with a plurality of holes and a porous elastic member such as polyurethane foam or the like disposed around the hollow pipe. The hollow pipe is filled with the paste. Then, the paste is extruded from the pipe to be coated on an inside surface 102 of the electrolyte member 10 through the porous elastic member within the inside space 100 of the electrolyte member 10. After coating the paste, the solid electrolyte member 10 is baked so that the paste is baked. As a result, the reaction electrode can be obtained. The above-mentioned method is disclosed, for example, in JP-A-52-94195.

JP-A-55-141665 discloses another method for manufacturing an $O_2$ sensor element. In the method, a tapered cup-type solid electrolyte member having an inside space, which is provisionally baked or finally baked, is prepared. The inside space of the electrolyte member is filled with a paste in advance. Then, a masking jig designed to have a shape approximately the same as that of the inside space and having a concave portion corresponding to a reaction electrode that is to be formed is inserted into the inside space of the electrolyte member. In this state, a fluid pressure is applied into the inside space of the electrolyte member through the masking jig. Accordingly, the paste invades a gap between the concave portion of the masking jig and the inside surface of the electrolyte member. As a result, the paste is coated on the inside surface of the electrolyte member at the concave portion to form a reaction electrode formation portion. Finally, the solid electrolyte member is baked so that the paste is baked, and thereby the reaction electrode can be formed.

However, the above-mentioned methods have the following problems. Firstly, in both methods, as shown in FIG. 1, the reaction electrode 92 is formed not only on the portion facing the heating portion 190 but on a bottom face 103 of the electrolyte member 10 as well. The bottom face 103 does not face the heating portion 190, so that the bottom face 103 is unlikely to be sufficiently heated. Further, it is difficult that a reference gas such as air circulates around the bottom face 103. Therefore, the reaction electrode 92 needs not be formed on the bottom face 103 of the electrolyte member 10. In addition, forming the reaction electrode 92 on the bottom face 103 increases material cost for that.

Next, when the electrolyte member 10 is provisionally or finally baked, a baking temperature is liable to have variations, resulting in variations in size of the electrolyte member 10. In such a case, in the former method, when the above-mentioned polyurethane foam is inserted into the inside space 100 of the electrolyte member 10 to supply the paste therefrom, a pressure applied to the polyurethane foam and the like is changed, so that an amount of the paste supplied from the polyurethane foam has variations. This makes difficult that the reaction electrode 92 has a uniform thickness. In the later method in which the masking jig is used, the gap between the masking jig and the inside surface 102 of the electrolyte member 10 becomes non-uniform. This also makes difficult that the reaction electrode 92 has a uniform thickness. In addition, there arises a problem concerning workability for inserting or removing the jig into or from the electrolyte member 10.

Further, the above-mentioned polyurethane foam serving as the coating jig is designed to contact the inside surface 102 of the electrolyte member 10 when coating the paste. Because of this, unless the electrolyte member 10 is tapered so that the diameter thereof becomes large as it becomes close to the opening from the bottom face 103 thereof, the paste is attached to the entire area of the inside surface 102 of the electrolyte member 10 when the polyurethane foam is taken out from the electrolyte member 10. This kind of problem occurs likewise in the case where the masking jig is used. Therefore, in the both methods, the shape of the electrolyte member 10 is restricted, and thereby flexibility of design of the $O_2$ sensor element is restricted. Further, the about-mentioned polyurethane foam is susceptible to clogging. The clogging of the polyurethane foam also causes variations in thickness of the reaction electrode 92. Furthermore, there is a problem that an output lead portion need to be formed by another process. In a case where the inside electrode 92 is formed by a chemical plating method utilizing one of the about-mentioned methods, the same problems as mentioned above can occur.

SUMMARY OF THE INVENTION

The present invention has been made in view of the above-mentioned problems and an object of the present invention is to provide a method and an apparatus for manufacturing an $O_2$ sensor element having a solid electrolyte member with high design flexibility. Another object of the present invention is to provide a method and an apparatus for manufacturing an $O_2$ sensor element in which an inside electrode is formed on a required portion of an inside surface of a solid electrolyte member with a required uniform thickness.

In order to achieve these and other objects of the present invention, a method for forming an inside electrode within a cup-type solid electrolyte member of an $O_2$ sensor element is provided. In the method, a nozzle having a paste discharge hole is inserted into an inside space of the electrolyte member, and the paste discharge hole of the nozzle is relatively rotated with respect to the electrolyte member along an inside surface of the electrolyte member. The paste discharge hole discharges the paste onto the inside surface of the electrolyte member while relatively rotating with respect to the electrolyte member. Then, by baking the electrolyte member, the inside electrode having a specific and uniform thickness can be formed on a required portion of the inside surface of the electrolyte member. The thickness of the inside electrode can be controlled by controlling an amount of the paste discharged from the nozzle, a relative rotational speed between the paste discharge hole and the electrolyte member, and the like. Further, this method does not restrict the shape of the electrolyte member, resulting in high design flexibility of the $O_2$ sensor element.

When relatively rotating the paste discharge hole of the nozzle, one of the paste discharge hole and the electrolyte member may rotate, and both of them may rotate with respect to each other. At the same time, the nozzle may be moved toward the opening of the inside space of the electrolyte member. Accordingly, the area of the inside electrode is not restricted by the shape of the nozzle. Further, the area of the inside electrode can be controlled arbitrary in an axial direction of the electrolyte member.

When removing the nozzle from the electrolyte member, the paste discharge hole may be moved toward the opening of the inside space of the electrolyte member while discharging the paste onto the inside surface of the electrolyte member. Accordingly, a lead formation portion that is to be a lead portion of the inside electrode after being baked can be formed with a uniform thickness. In this case, the thickness of the lead portion can be controlled by controlling a relative moving speed between the paste discharge hole and the electrolyte member and the like.

In order to achieve the above-mentioned objects of the present invention, an apparatus for forming an inside electrode on an inside surface of a cup-type solid electrolyte member of an $O_2$ sensor element is also provided. The apparatus includes an electrolyte holder for holding the electrolyte member and adjusting a position of the electrolyte member, a nozzle having a paste discharge hole for discharging paste, and a nozzle holder for holding the nozzle and inserting the nozzle into an inside space of the electrolyte member held by the electrolyte holder. Further, one of the electrolyte holder and the nozzle holder can rotate with respect to the other one. By employing this apparatus, the above-mentioned effects can be easily obtained.

BRIEF DESCRIPTION OF THE DRAWINGS

These and other objects and features of the present invention will become more readily apparent from a better understanding of preferred embodiments described below with reference to the following drawings.

FIGS. 8A and 8B are cross-sectional views for indicating states of the reaction electrode formation portion during the processes shown in FIGS. 7A to 7D;

FIG. 9 is a graph showing variations in thickness of inside electrodes of $O_2$ sensor elements in accordance with positions of the inside electrodes in the first embodiment;

DETAILED DESCRIPTION OF THE PREFERRED EMBODIMENTS

Embodiments according to the present invention will be described herein under with reference to the drawings.

First Embodiment

Figure 1:
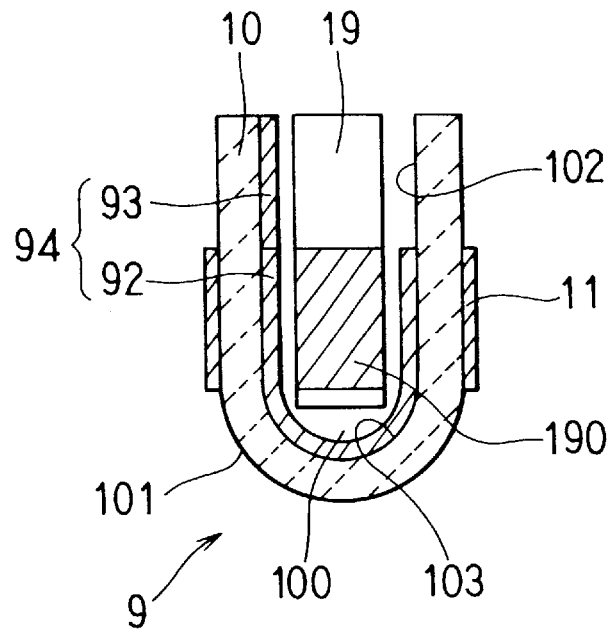
FIG. 1 is a cross-sectional view showing a main part of an $O_2$ sensor element according to a prior art.

A method for manufacturing an $O_2$ sensor element 1 in a first preferred embodiment will be explained referring to FIGS. 2 to 10. The $O_2$ sensor element 1 is an oxygen concentration electromotive force type element used for an A/F control for an internal combustion engine of a vehicle, which can detect an oxygen concentration in an exhaust gas. The parts and components similar to those shown in FIG. 1 are shown by the same reference numerals.

Figure 2:
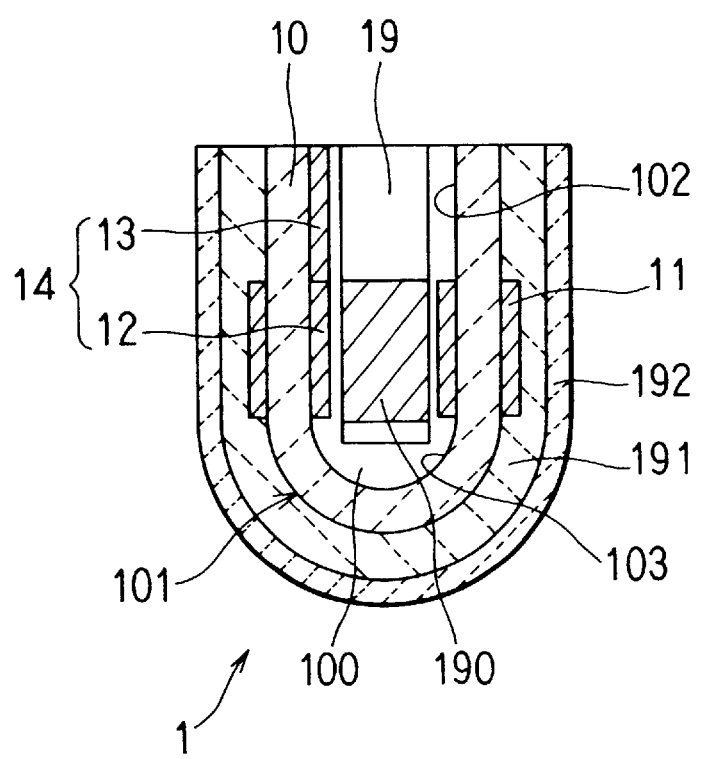
FIG. 2 is a cross-sectional view showing a main part of an $O_2$ sensor element in a first preferred embodiment of the present invention.

As shown in FIG. 2, the $O_2$ sensor element 1 has a cup-type solid electrolyte member 10 having an inside space 100 therein and an opening at an end thereof, an outside electrode 11 formed on an outside surface 101 of the electrolyte member 10, and an inside electrode 14 formed on an inside surface 102 of the electrolyte member 10 within the inside space 100. The inside electrode 14 further composed of a reaction electrode 12 and a lead portion 13. The electrolyte member 10 is made of $ZrO_2$ containing yttrium oxide ($Y_2O_3$) of 4 mol % to 6 mol %. The inside electrode 14 is made of Pt, palladium (Pd), rhodium (Rh), or the like, or those mixture added with metallic oxide powder having oxygen ion conductivity. The outside electrode 11 is made of the same material as that of the inside electrode 14. The outside electrode 11 is covered with a porous protection layer 191 made of metallic oxide such as $MgO \cdot Al_2O_3$ having a spinel structure, or the like. Further, the surface of the protection layer 192 is covered with a porous poison trap layer 192 made of $\gamma$-$Al_2O_3$ or the like.

In addition, a heater 19 is disposed in the inside space 100 of the electrolyte member 10. The heater 19 has a heating portion 190 for heating upon receiving electricity. The reaction electrode 12 of the above-mentioned inside electrode 14 is disposed on the inside surface 102 of electrolyte member 10 to face the heating portion 190 of the heater 19. The outside electrode 11 is disposed on the outside surface 101 of the electrolyte member 10 to face the reaction electrode 12 through the electrolyte member 10.

Figure 3:
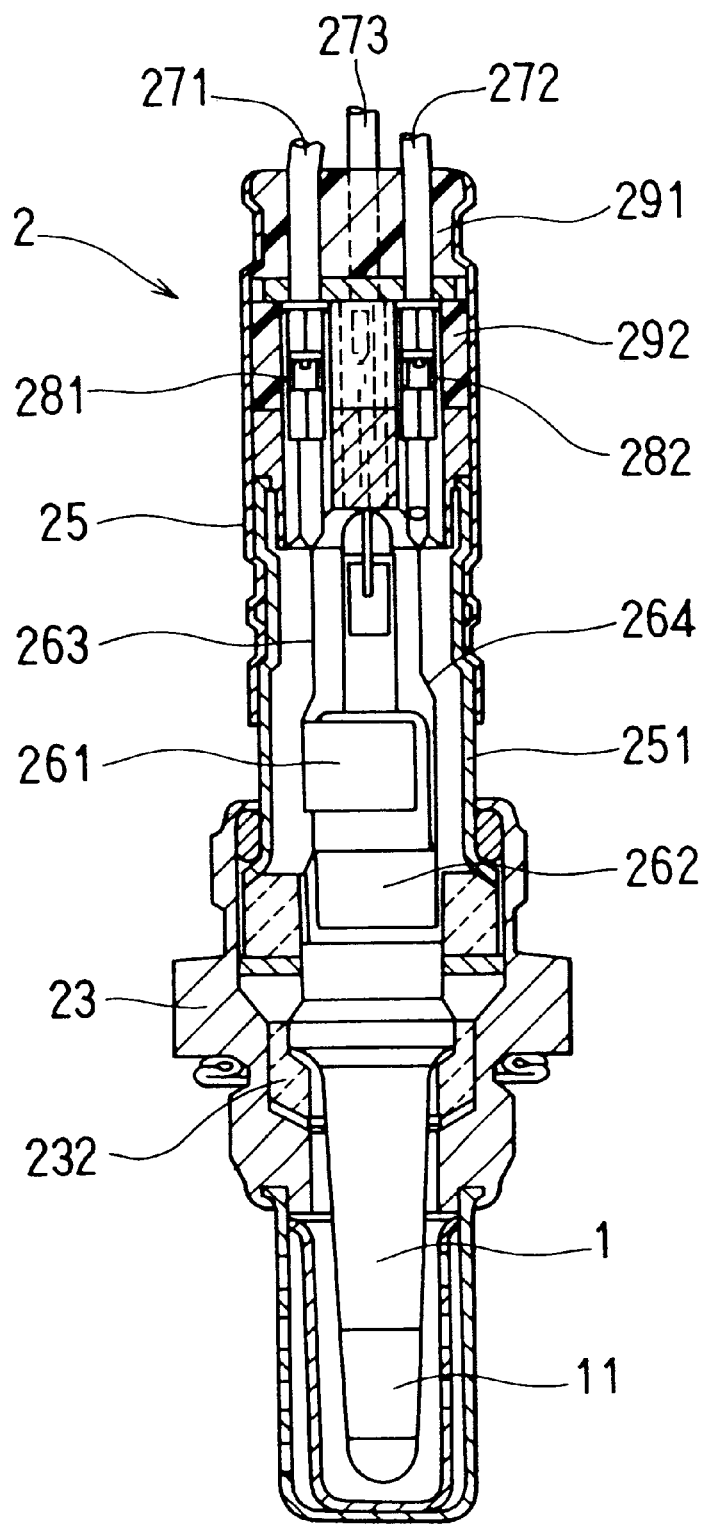
FIG. 3 is a cross-sectional view showing an $O_2$ sensor holding the $O_2$ sensor element shown in FIG. 2.

Next, an $O_2$ sensor 2 in which the $O_2$ sensor element 1 is installed will be explained. As shown in FIG. 3, the $O_2$ sensor 2 has a cylindrically shaped metallic housing 23, and the $O_2$ sensor element 1 is fixed to the inside surface of the housing 23 via an insulation material 232. In the $O_2$ sensor 2, a cover body 251 is fixed to an upper portion of the housing 23 in FIG. 3 at an end thereof, and a cover 25 for covering insulation elastic members 291 and 292 is fixed to the other end of the cover body 251. Four of output lead wires 271, 272, heater lead wires 273, 274 are taken out from the $O_2$ sensor 2 through the insulation elastic member 291. Here, the lead wire 274 is not shown in FIG. 3.

The output lead wires 271, 272 are respectively and electrically connected to the above-mentioned outside and inside electrodes 11, 14 of the $O_2$ sensor element 1 through connectors 281, 282, electrode lead portions 263, 264 and plate springs 261, 262. The heater lead wires 273, 274 are electrically connected to the heater 19 held within the inside space 100 of the $O_2$ sensor element 1.

Next, a method for manufacturing the $O_2$ sensor element 1 will be explained in detail. Firstly, after forming powder of $ZrO_2$ containing $Y_2O_3$ of 5 mol %, a cup-like body is formed from the powder and is provisionally baked at 1000° C.–1200° C., thereby forming the solid electrolyte member 10. On the other hand, a conductive paste for forming the outside and inside electrodes 11, 14 are prepared by mixing Pt, the $ZrO_2$ powder that is the same one as that for the solid electrolyte member 10, resin material, and solvent. The viscosity of the conductive paste is controlled to be in a range of 5 Pa·s to 30 Pa·s.

Figure 7A:
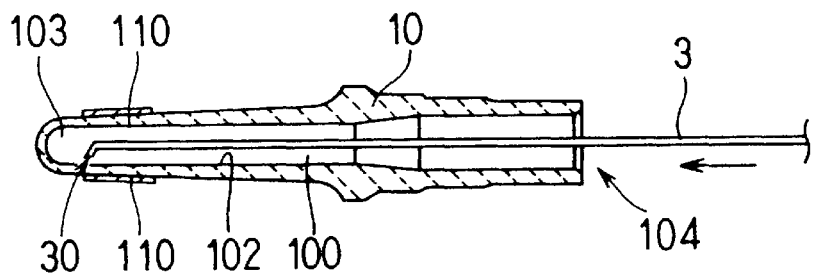
FIGS. 7A to 7D are cross-sectional views for explaining processes for forming a reaction electrode formation portion and a lead formation portion in the $O_2$ sensor element in the first element.

Next, the conductive paste is coated on the outside surface 101 of the solid electrolyte member 10 by pad-printing at a position corresponding to a position where the heating portion 190 of the heater 19 is to be disposed in the solid electrolyte member 10 (refer to FIG. 7A). Accordingly, an outside electrode formation portion 110 are formed. The outside electrode formation portion 110 is contracted at 20% thereof in a main baking process. Therefore, the outside electrode formation portion 110 is formed previously to have a length in an axial direction of the electrolyte member 10 longer than that of the heating portion 190 at approximately 20% on the position capable of securely facing the heating portion 190 after the main baking process. The outside electrode formation portion 110 is dried at 120° C. for 30 minutes after being coated.

Then, a method for forming a reaction electrode formation portion 120 and a lead formation portion 130, that is, an inside electrode formation portion for forming the inside electrode 14 will be explained.

Figure 4:
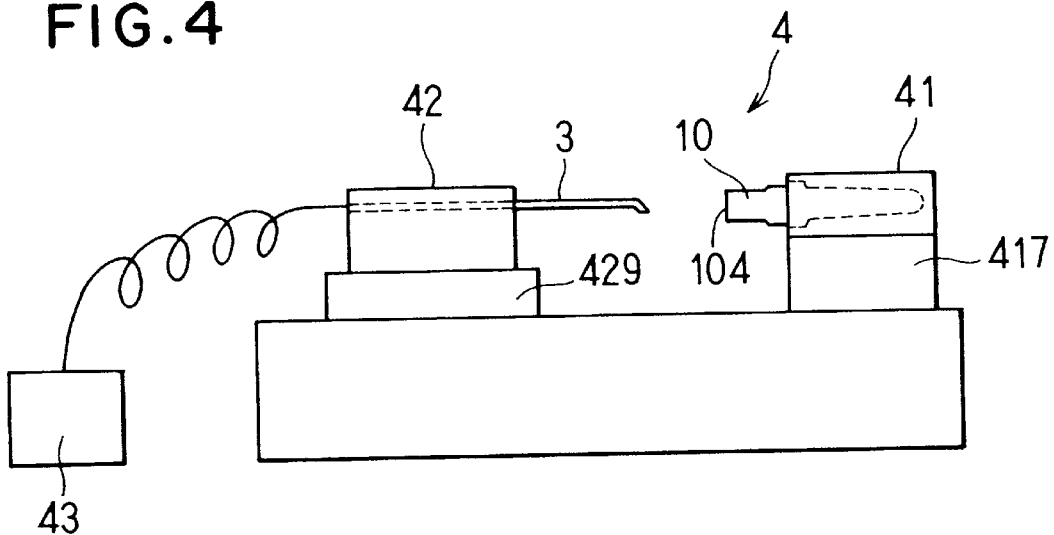
FIG. 4 is a side view showing an apparatus used for manufacturing the $O_2$ sensor element in the first embodiment.

Firstly, an apparatus 4 used for forming the reaction electrode formation portion 120 and the lead formation portion 130 will be explained. As shown in FIG. 4, the apparatus 4 has a cylinder-type holder (electrolyte holder) 41 for movably holding the solid electrolyte member 10, a nozzle 3 for being inserted into the inside space 100 of the electrolyte member 10 and for supplying the paste for forming the inside electrode 14 within the inside space 100, and a nozzle holder 42 for movably holding the nozzle 3. The cylinder-type holder 41 can rotate with respect to the nozzle holder 42. The nozzle 3 communicates with a paste supply device 43 holding the paste therein. In FIG. 4, reference numeral 429 indicates a movable stage for advancing or retreating the nozzle 3, and reference numeral 417 indicates an arm for raising or lowering the solid electrolyte member 10.

Figure 5A:
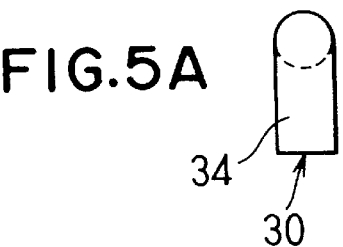
FIG. 5A is a front view showing a nozzle used for the apparatus shown in FIG. 4.
Figure 5B:
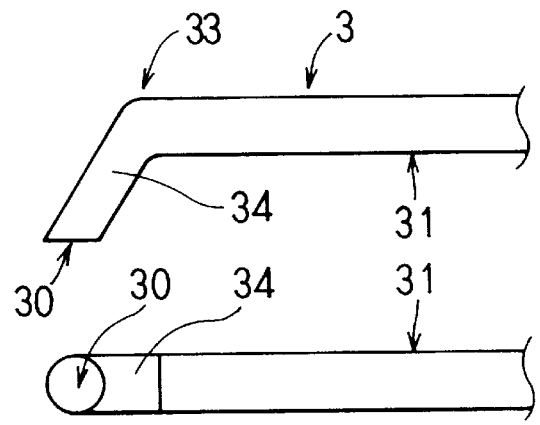
FIG. 5B is a side view showing the nozzle shown in FIG. 5A.
Figure 5C:
FIG. 5C is a bottom view showing the nozzle shown in FIGS. 5A and 5B.
Figure 6A:
FIG. 6A is a front view showing a modified nozzle used for the apparatus shown in FIG. 4.
Figure 6B:
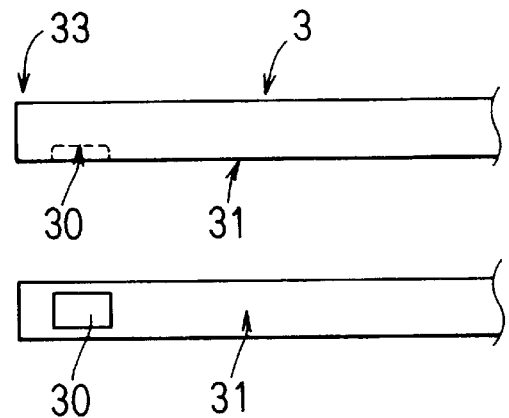
FIG. 6B is a side view showing the nozzle shown in FIG. 6A.
Figure 6C:
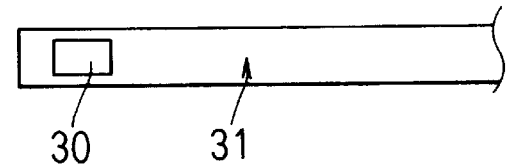
FIG. 6C is a bottom view showing the nozzle shown in FIGS. 6A and 6B.

An internal diameter of the nozzle 3 is 1.0 mm. As shown in FIGS. 5A to 5C, the nozzle 3 has a bent portion 34 formed at a front end portion 33 thereof, and a paste discharge hole 30 is provided at an end of the bent portion 34. However, the structure of the nozzle 3 is not limited to that shown in FIGS. 5A to 5C, and the nozzle 3 may have a structure shown FIGS. 6A to 6C. The nozzle 3 shown in FIGS. 6A to 6C does not have the above-mentioned bent portion 34, and the paste discharge hole 30 is formed in a front end side face 31.

Then, processes for forming the reaction electrode formation portion 120 and the lead formation portion 130 will be explained. Firstly, the solid electrolyte member 10 is fixed to the holder 41 of the apparatus 4 as shown in FIG. 4. Then, the nozzle holder 42 is advanced so that the nozzle 3 is inserted into the electrolyte member 10 through an opening 104 of the inside space 100 until the paste discharge hole 30 faces the outside electrode formation portion 110 around a bottom face 103 of the electrolyte member 10 through the electrolyte member 10 as shown in FIG. 7A.

Figure 7B:
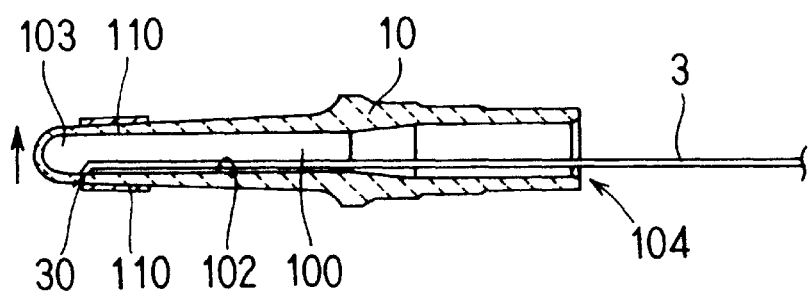
Figure 7C:
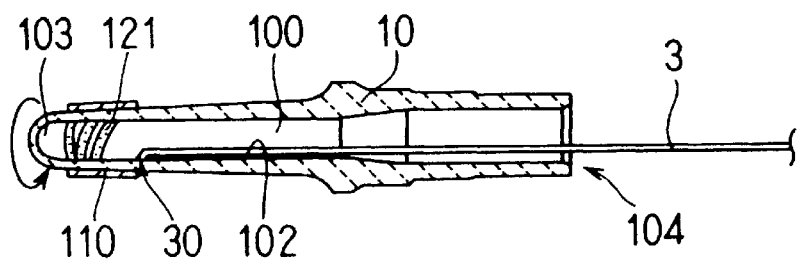

Next, the arm 417 is lengthened to raise the electrolyte member 10 until the inside surface 102 of the electrolyte member 10 contacts the paste discharge hole 30 of the nozzle 3 as shown in FIG. 7B. Then, the paste is supplied to the nozzle 3 from the past supply device 43. As soon as the paste is discharged from the paste discharge hole 30, the electrolyte member 10 is rotated as shown in FIG. 7C. At the same time, the paste discharge hole 30 of the nozzle 3 starts to move toward the opening 104 of the inside space 100 in the axial direction of the electrolyte member 10. In this case, a relative moving speed between the nozzle 3 and the electrolyte member 10 is 3 mm/s. Accordingly, as shown in FIGS. 8A, a reaction electrode formation portion 121 having a spiral contour is formed. In this process, a relative rotational frequency between the nozzle 3 and the electrolyte member 10 is set to be 150 r.p.m, and does not change by time. A discharge amount of the paste is set to be approximately 10 mg/sec., and does not change by time as well.

Figure 7D:
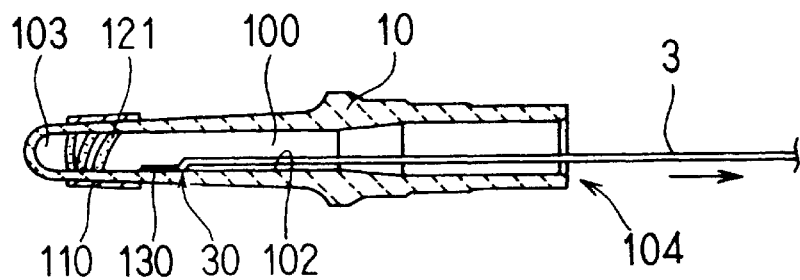

When the paste discharge hole 30 of the nozzle 3 reaches a specific portion, the rotation of the electrolyte member 10 is stopped. On the other hand, the retreat of the nozzle 3 from around the bottom face 103 of the inside space 100 toward the opening 104 is continued, while the supply of the paste from the paste discharge hole 30 is also continued as shown in FIG. 7D. At that time, a relative moving speed between the nozzle 3 and the electrolyte member 10 is approximately 40 mm/s. Accordingly, the lead formation portion 130 can be formed. The supply of the paste to the nozzle 3 is stopped when the paste discharge hole 30 of the nozzle 3 reaches the opening 104.

Thereafter, the electrolyte member 10 is dismounted from the apparatus 4, and then is dried at 120° C. for 30 minutes. The reaction electrode formation portion 121 having the spiral contour shown in FIG. 8A is flattened by sagging the paste during the dry process as shown in FIG. 8B, thereby forming the reaction electrode formation portion 120 having a flat surface. Here, it should be noted that a length of the thus formed reaction electrode formation portion 120 in the axial direction of the electrolyte member 10 is different from a length M (see FIG. 10) of the reaction electrode 12 after baked. This is because the reaction electrode formation portion 120 is contracted at approximately 20% by baking. Successively, the electrolyte member 10 is set in a baking furnace, and is finally baked at a temperature of 1500° C.–1600° C. As a result, the paste forming the outside electrode formation portion 110, the reaction electrode formation portion 120, and the lead formation portion 130 is baked, so that the outside and inside electrodes 11, 14 can be obtained.

Next, the protection layer 191 is formed on the surface of the outside electrode 11 by a plasma spraying method using $MgO \cdot Al_2O_3$ having a spinel structure or the like. Further, slurry including $\gamma$-$Al_2O_3$ powder is dipped on the surface of the protection layer 191, and then is baked. Accordingly, the poison trap layer 192 is formed. Finally, as shown in FIGS. 2 and 3, the heater 19 is inserted into the inside space 100 of the electrolyte member 10. As a result, the $O_2$ sensor element 1 in this embodiment is completed.

Figure 10:
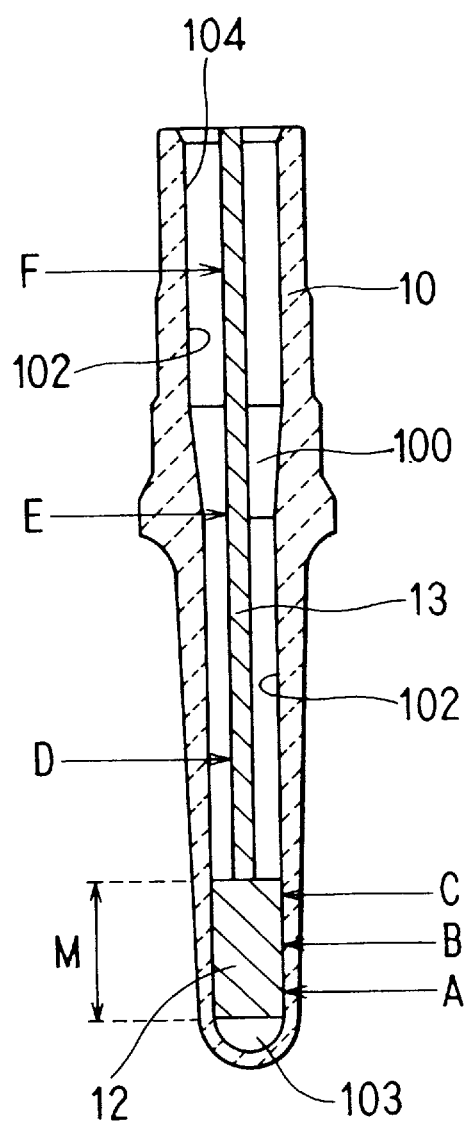
FIG. 10 is a cross-sectional view showing positions of the inside electrode where thicknesses are measured to obtain the graph of FIG. 9.

In the thus obtained $O_2$ sensor element 1, variations in thickness of the inside electrode 14 were evaluated. The results are plotted in FIG. 9. Specifically, thirty $O_2$ sensor elements 1 manufactured by the above-mentioned method were prepared. Then, each cross-section of inside electrodes 14 of the $O_2$ sensor elements 1 was observed by scanning electron microscope (SEM) and was photographed. Thicknesses of the inside electrodes 14 of the $O_2$ sensor elements 1 were measured using the photographs of SEM. Measured positions of the thicknesses in one $O_2$ sensor element 1 are shown in FIG. 10, in which six measured positions are indicated by A to F. In FIG. 9, each point indicates an average value of thicknesses of the inside electrodes 14 of the thirty $O_2$ sensor elements 1 measured at the same position of A to F shown in FIG. 10. Each line segment including a corresponding one point on a center thereof indicates variations of $\pm 3\sigma$ of the thicknesses.

According to FIG. 9, it is confirmed that the variations in thickness of the inside electrode 14 can be decreased on the entire area of the inside electrode 14 by adopting the manufacturing method in this embodiment. In a conventional method accompanying large variations in thickness of the inside electrode, the inside electrode is formed to entirely have a relatively thick thickness so that a minimum necessary thickness can be secured even at the thinnest portion thereof. As opposed to this, in this embodiment, because the variations in thickness of the inside electrode 14 is very small, the inside electrode 14 can be formed with a required thickness. That is, the inside electrode 14 can be formed with a thickness thinner than that in the prior art. Accordingly, an amount of the paste for the electrode can be reduced.

Next, these and the other effects in this embodiment will be explained in more detail. In the above-mentioned method, the paste discharge hole 30 of the nozzle 3 is relatively rotated at the position close to the bottom face 103 of the electrolyte member 10 while being retreated in the axial direction of the electrolyte member 10. As a result, the reaction electrode formation portion 120 can be formed. The paste discharge hole 30 of the nozzle 3 is further moved relative to the electrolyte member 10 in the axial direction of the electrolyte member 10. As a result, the lead formation portion 130 can be formed.

Accordingly, the reaction electrode 120 can be formed only on the position facing the heating portion 190 of the heater 19 inserted into the inside space 100. Therefore, the amount of the paste can be suppressed at the minimum necessary value, thereby decreasing material cost. In addition, in the above-mentioned method, the discharge amount of the paste is controlled to be constant. Further, the rotational speed of the electrolyte member 10 and the relative moving speed in the axial direction between the paste discharge hole 30 and the electrolyte member 10 are constant so that the discharge amount of the paste is constant. Therefore, the reaction electrode formation portion 120 and the lead formation portion 130 can be formed easily to have a required and uniform thickness, and therefore the inside electrode 14 can have a required and uniform thickness. That is, by controlling the relative rotational speed and the relative moving speed between the nozzle and the electrolyte member 10, the thickness of the inside electrode 14 can be controlled.

The above-mentioned nozzle 3 has an external diameter smaller than that of the inside space 100 of the electrolyte member 10, and the paste discharge hole 30 of the nozzle 3 is provided only on the front end side face 31. Accordingly, the nozzle 3 can be removed from the inside space 100 without attaching the paste to unnecessary portions of the inside surface 102 of the electrolyte member 10. It is not necessary that the nozzle has a shape corresponding to the shape of the inside surface of the electrolyte member. Accordingly, the shape of the electrolyte member 10 of the $O_2$ sensor element 1 can be flexibly designed, and can be changed in accordance with objects, the shape of the $O_2$ sensor 2 in which the $O_2$ sensor element 1 is installed, and the like.

Second Embodiment

Figure 11A:
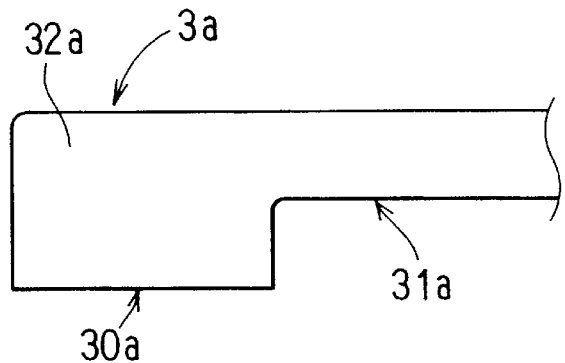
FIG. 11A is a side view showing a nozzle used in a second preferred embodiment.
Figure 11B:
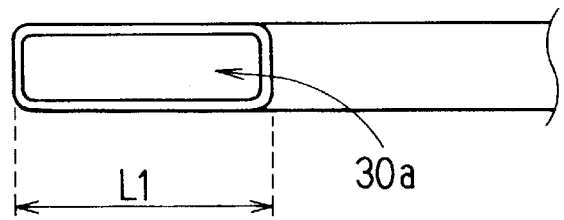
FIG. 11B is a bottom view showing the nozzle shown in FIG. 11A.

In a second preferred embodiment, it is featured that a nozzle 3a shown in FIGS. 11A to 11C is used to form the reaction electrode formation portion 120 and the lead formation portion 130 in place of the nozzle 3 in the first embodiment. The apparatus 4 used in the first embodiment is used in the second embodiment as well. The parts and components similar to those in the first embodiment are shown by the same reference numerals and descriptions thereof will be omitted.

Figure 12A:
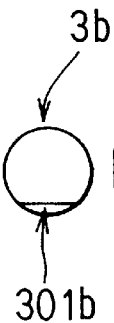
FIG. 12A is a front view showing a modified nozzle in the second embodiment.
Figure 12B:
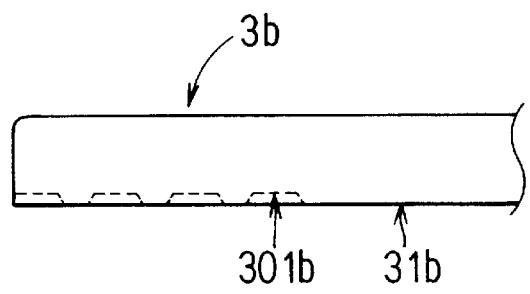
FIG. 12B is a side view showing the nozzle shown in FIG. 12A.
Figure 12C:
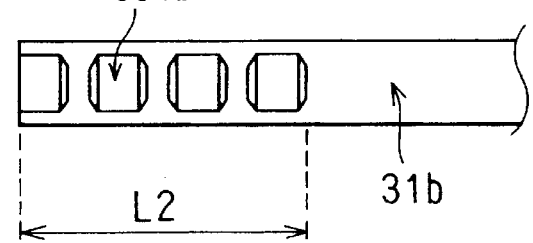
FIG. 12C is a bottom view showing the nozzle shown in FIGS. 12A and 12B.

The nozzle 3a used in the second embodiment has a protruding portion 32a at a front end portion thereof, and a paste discharge hole 30a is provided at an end of the protruding portion 32a. The paste discharge hole 30a has a generally rectangular shape. A length L1 of the paste discharge hole 30a in an extending direction of the nozzle 3a is substantially the same as that of the reaction electrode formation portion 120 that is to be coated by the nozzle 3a. In this embodiment, in place of the nozzle 3a shown in FIGS. 11A to 1C, a nozzle 3b shown in FIGS. 12A to 12C may be used. The nozzle 3b has several paste discharge holes 301b arranged on a front end side face 31b in an extending direction of the nozzle 3b. In this case, a length L2 between both ends of all the several paste discharge holes 301b is set to be substantially the same as that of the reaction electrode formation portion 120.

Next, the manufacturing method using the nozzle 3a will be briefly explained. As in the first embodiment, after forming the solid electrolyte member 10, the outside electrode formation portion 110 is formed on the outside surface of the electrolyte member 10. Then, the electrolyte member 10 is fixed to the cylinder-type holder 41 of the apparatus 4 as shown in FIG. 5. These processes are the same as those in the first embodiment.

Figure 13A:
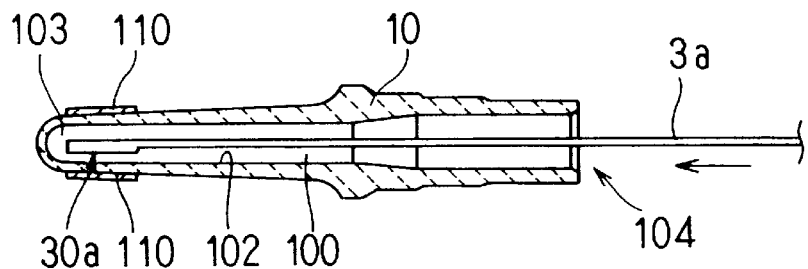
FIGS. 13A to 13D are cross-sectional views for explaining processes for forming a reaction electrode formation portion and a lead formation portion of an $O_2$ sensor element in the second embodiment.

In the second embodiment, the nozzle holder 42 shown in FIG. 5 holds the above-mentioned nozzle 3a. Then, the nozzle holder 42 is advanced to insert the nozzle 3a into the inside space 100 through the opening 104. Accordingly, the nozzle 3a is inserted into the space 100 until an end of the paste discharge hole 30a on a front side thereof corresponds to an end portion of the outside electrode formation portion 110 close to a bottom face 103 of the electrolyte member 10 as shown in FIG. 13A.

Figure 13B:
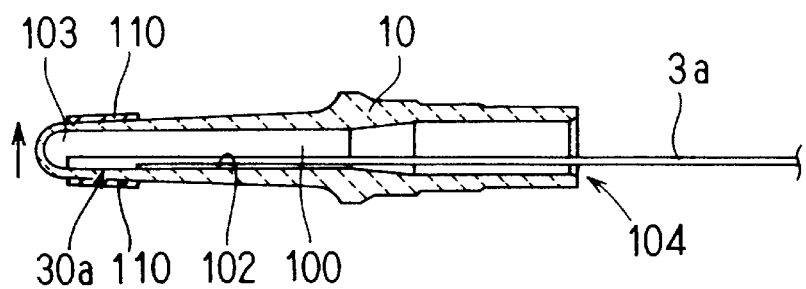
Figure 13C:
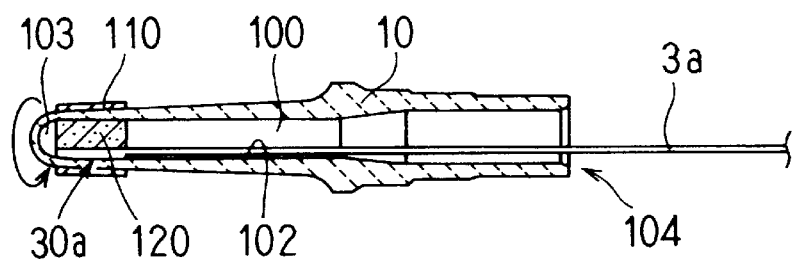
Figure 13D:
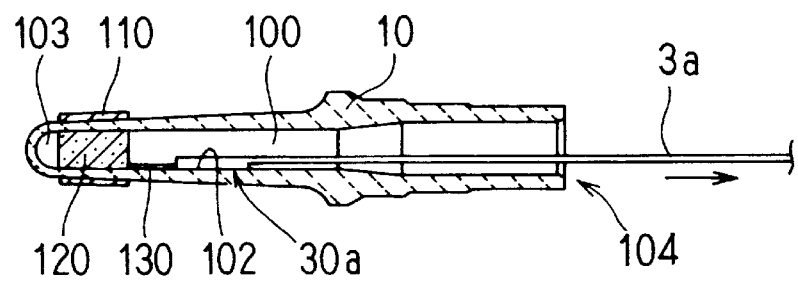

Next, the arm 417 (see FIG. 5) is stretched to raise the electrolyte member 10 so that the paste discharge hole 30a contacts the inside surface 102 of the electrolyte member 10 as shown in FIG. 13B. In this state, the paste is supplied to the nozzle 3a from the paste supply device 43. As soon as the paste is discharged from the paste discharge hole 30a, the electrolyte member 10 is rotated as shown in FIG. 13C. Accordingly, the reaction electrode formation portion 120 is obtained. Then, after stopping the rotation of the electrolyte member 10, the nozzle 3a is retreated from the bottom face 103 to the opening 104 within the inside space 100 while supplying the paste from the paste discharge hole 30a as shown in FIG. 13A. As a result, the lead formation portion 130 is obtained. The successive other processes are similar to those in the first embodiment.

In the second embodiment, the reaction electrode formation portion 120 can be formed only by one rotation of the electrolyte member 10. The other effects are the same as in the first embodiment. In the second embodiment, it is not always necessary that the nozzle 3a and the inside surface 102 of the electrolyte member 10 contact each other when forming the reaction electrode formation portion 120. The nozzle 3a and the inside surface 102 of the electrolyte member 10 can make a space therebetween, or partially contact each other.

In the first and second embodiments, although the electrolyte member 10 rotates with respect to the nozzle to form the reaction electrode formation portion 120, the nozzle may rotate with respect to the electrode body 10. Further, both of the nozzle and the electrolyte member may be rotate with respect to each other.

The relative rotational frequency between the nozzle and the electrolyte member is preferably in a range of 5 r.p.m to 300 r.p.m. When the relative rotational frequency is smaller than 5 r.p.m., a thickness of the reaction electrode 12 becomes too thick for oxygen to reach a three phase boundary point. Consequently, there arise a possibility that an oxygen deficiency phenomenon occurs. On the other hand, when the relative rotational frequency is larger than 300 r.p.m., it is difficult that the above-mentioned paste is stably attached to the inside surface of the electrolyte member, resulting in variations in thickness of the reaction electrode 12.

When forming the reaction electrode formation portion 120 by relatively rotating the nozzle with respect to the electrolyte member 10, it is preferable that the relative moving speed between the nozzle and the electrolyte member 10 is in a range of 0.5 mm/s to 20 mm/s. When the relative moving speed is smaller than 0.5 mm/s, the discharge amount of the paste is increased, so that the paste coated on the inside surface of the electrolyte member 10 is liable to flow to unnecessary portions. The paste on the unnecessary portions of the inside surface can cause deficiencies. When the relative moving speed is larger than 20 mm/s, it is difficult that the above-mentioned paste is stably attached to the inside surface of the electrolyte member, resulting in variations in thickness of the reaction electrode formation portion 120.

On the other hand, when forming the lead formation portion 130, it is preferable that the relative moving speed between the nozzle and the electrolyte member is preferably in a range of 0.5 mm/s–100 mm/s. When the relative moving speed is smaller than 0.5 mm/s, the thickness of the lead portion becomes thick to increase material cost. When the relative moving speed is larger than 100 mm/s, it is difficult that the above-mentioned paste is stably attached to the inside surface of the electrolyte member, resulting in variations in thickness of the lead portion 13.

As mentioned above, the viscosity of the conductive paste is preferably in a range of 5 Pa·s to 30 Pa·s. When the viscosity is smaller than 5 Pa·s, there arises a possibility that the paste coated on the inside surface of the electrolyte member flows before being dried. This makes difficult that the inside electrode 14 has a specific shape. On the other hand, when the viscosity is larger than 30 Pa·s. the paste cannot be stably discharged from the paste discharge hole of the nozzle. This also causes variations in thickness of the inside electrode 14.

The above-mentioned paste includes at least one of Pt, Pd, and Rh, added with resin and solvent. The paste may include metallic oxide powder having oxygen ion conductivity. For example, the paste including Pt of 46 wt %, the $ZrO_2$ powder, which is the same material as that of the electrolyte member 10, of 4 wt %, and resin and solvent of 50 wt % can be used.

The nozzle used in the above-mentioned embodiments preferably has an internal diameter in a range of 0.3 mm–3 mm. In the case where the internal diameter of the nozzle is smaller than 0.3 mm, the nozzle is liable to be clogged with the paste. In the case where the internal diameter of the nozzle is larger than 3 mm, the discharge amount of the paste from the nozzle becomes unstable, resulting in variations in thickness of the inside electrode 14.

In the first and second embodiments, because the conductive paste is baked along with the electrolyte member 10, the obtained $O_2$ sensor element can have sufficient heat resistance.

Third Embodiment

In a third preferred embodiment, an inside electrode is formed by a chemical plating process. In the third embodiment, the manufacturing apparatus 4 shown in FIG. 5 is used as in the first embodiment, and the processes using the apparatus 4 are also generally the same as those in the first embodiment except that a paste that is to be coated on an electrolyte member 10 serves as an activation paste for helping chemical plating reaction to start in the chemical plating process. That is, processes for forming a reaction electrode formation portion and a lead formation portion in this embodiment corresponds to activation processes previous to the chemical plating process. The activation paste contains at least one of Pt, Pd, Au, and Rh. For example, a paste composed of a Pt containing organic compound of 0.4 wt %, and resin and solvent of 99.6 wt % can be used as the activation paste.

Next, a method for manufacturing an $O_2$ sensor element in the third embodiment will be explained in more detail. Firstly, the solid electrolyte member 10 is formed in the same way as in the first embodiment. Here, it should be noted that in the third embodiment, in this state, a final (main) baking process is performed on the electrolyte member 10. Then, an outside electrode formation portion are formed on an outside surface 101 of the electrolyte member 10.

Subsequently, the same process as explained referring to FIGS. 7A to 7D in the first embodiment are performed on the electrolyte member 10, thereby forming the reaction electrode formation portion and the lead formation portion. Preferable conditions for forming the reaction electrode formation portion and the lead formation portion are the same as those in the first and second embodiments. Thereafter, the electrolyte member 10 is heated at 300° C.–500° C. Accordingly, the about-mentioned outside electrode formation portion, the reaction electrode formation portion, and the lead formation portion are metallized to form activation portions 119, 129, and 139 shown in FIG. 14.

Figure 14:
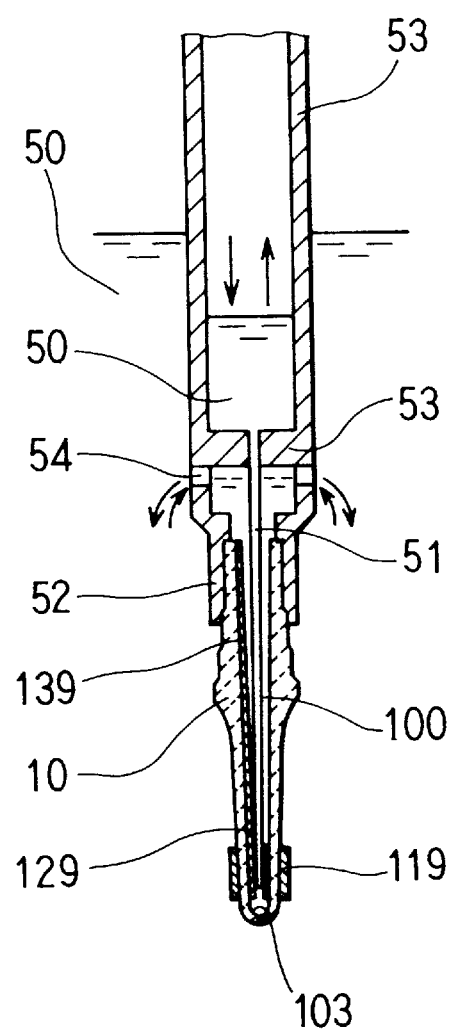
FIG. 14 is a view showing a process for chemically plating an solid electrolyte member in a third preferred embodiment.

Then, the chemical plating process is performed on the activation portions 119, 129, and 139. Specifically, as shown in FIG. 14, the electrolyte member 10 is inserted into a holder 53 of a plating jig at a lower end 52 of the holder 53, and then is fixed to the holder 53. At that time, it is necessary that an inhalation needle 51 protruding form the holder 53 is provided at a position close to the bottom face 103 within the inside space 100 of the electrolyte member 10.

In this state, the electrolyte member 10 is immersed in a plating bath filled with plating liquid 50. The inside space 100 of the electrolyte member 10 communicates with the plating bath through narrow holes 54. Then, air within the holder 53 is attracted. Accordingly, air within the inside space 100 is absorbed into the holder 53 through the inhalation needle 53, and accordingly, the plating liquid 50 is absorbed into the inside space from the plating bath through the narrow holes 54 and then into the holder 53 through the inhalation needle 53. By performing this process, the inside space 100 is filled with the plating liquid 50, and then the plating liquid 50 attaches to the activation portions 129 and 139.

Thereafter, air is introduced into the holder 53. Accordingly, the plating liquid 50 within the holder 53 is discharged from the inhalation needle 51, and the plating liquid within the inside space 100 is discharged into the plating bath through the narrow holes 54. By repeating the above-mentioned processes several times, a chemical plating layer having a required thickness can be formed on the activation portions 129 and 139. Because these processes are performed in the plating bath filled with the plating liquid 50, a chemical plating layer is formed on the activation portion 119 on the outside surface of the electrolyte member 10 as well.

After forming the chemical plating layers, the electrolyte member 10 is taken out from the plating bath, and is heated at 800° C.–1200° C. As a result, the plating layers are baked, thereby forming the outside and inside electrodes. The other features are the same as those in the first embodiment. According to the third embodiment, the inside electrode can be formed only on the required portion by utilizing the chemical plating process. The other effects are the same as those in the first embodiment.

Although the $O_2$ sensor element holding the heater therein is adopted in the above-mentioned embodiments, it is apparent that an $O_2$ sensor element without holding a heater may be adopted to obtain the same effects.

While the present invention has been shown and described with reference to the foregoing preferred embodiment, it will be apparent to those skilled in the art that changes in form and detail may be made therein without departing from the scope of the invention as defined in the appended claims.

What is claimed is:

1. A method for manufacturing an $O_2$ sensor element having a cup-shaped solid electrolyte member having an inside space with an opening, an outside electrode provided on an outside surface of the solid electrolyte member, and an inside electrode provided on an inside surface of the solid electrolyte member within the inside space, the method comprising steps of:

preparing a nozzle having a paste discharge hole at a front end thereof, the paste discharge hole being for discharging conductive paste for forming the inside electrode;

inserting the front end of the nozzle into the inside space of the solid electrolyte member;

relatively rotating the paste discharge hole of the nozzle with respect to the solid electrolyte member along the inside surface of the solid electrolyte member while discharging the paste from the paste discharge hole onto the inside surface of the solid electrolyte member;

removing the nozzle from the solid electrolyte member; and baking the solid electrolyte member.

2. The method of claim 1, wherein in the step of relatively rotating the paste discharge hole, at the same time, the paste discharge hole is moved toward the opening of the inside space of the electrolyte member.

3. The method of claim 1, wherein a heater is inserted into the inside space of the solid electrolyte member after baking the solid electrolyte member.

4. The method of claim 1, wherein in the step of relatively rotating the paste discharge hole with respect to the solid electrolyte member, one of the paste discharge hole and the solid electrolyte member rotates.

5. The method of claim 1, wherein in the step of relatively rotating the paste discharge hole with respect to the solid electrolyte member, both of the paste discharge hole and the solid electrolyte member rotate with respect to each other.

6. The method of claim 1, wherein the step of removing the nozzle includes a step of relatively moving the paste discharge hole of the nozzle with respect to the solid electrolyte member toward the opening of the inside space of the solid electrolyte member while discharging the paste to the inside surface of the solid electrolyte member.

7. The method of claim 6, wherein:
the inside electrode is composed of a reaction electrode and a lead portion;
a reaction electrode formation portion that is to be the reaction electrode after being baked is formed by the step of relatively rotating the paste discharge hole; and
a lead formation portion that is to be the lead portion after being baked is formed by the step of relatively moving the paste discharge hole toward the opening of the inside space.

8. The method of claim 7, wherein the step of relatively moving the paste discharge hole is performed after stopping rotation between the paste discharge hole and the electrolyte member.

9. The method of claim 6, wherein in the step of relatively moving the paste discharge hole toward the opening of the inside space, the paste discharge hole is relatively moved with respect to the solid electrolyte member in an axial direction of the solid electrolyte member.

10. The method of claim 6, wherein in the step of relatively moving the paste discharge hole toward the opening, one of the paste discharge hole and the solid electrolyte member is moved.

11. The method of claim 6, wherein in the step of relatively moving the paste discharge hole toward the opening, both of the paste discharge hole and the solid electrolyte member are moved with respect to each other.

12. The method of claim 1, wherein an inside electrode formation portion that is to be the inside electrode after being baked is formed to have a spiral shape on the inside surface of the solid electrolyte member by the step of relatively rotating the paste discharge hole with respect to the solid electrolyte member.

13. A method for manufacturing an $O_2$ sensor element having a cup-shaped solid electrolyte member having an inside space with an opening, an outside electrode provided on an outside surface of the solid electrolyte member, and an inside electrode provided on an inside surface of the solid electrolyte member within the inside space, the method comprising steps of:
preparing a nozzle having a paste discharge hole at a front end thereof, the paste discharge hole being for discharging paste including activation material for helping chemical plating reaction to start;
inserting a front end of the nozzle into the inside space of the solid electrolyte member;
relatively rotating the paste discharge hole of the nozzle with respect to the solid electrolyte member along the inside surface of the solid electrolyte member while discharging the paste from the paste discharge hole onto the inside surface of the solid electrolyte member to thereby form an inside electrode formation portion on which the inside electrode is to be formed;
removing the nozzle from the solid electrolyte member;
injecting a chemical plating liquid into the inside space of the solid electrolyte member; and
performing chemical plating on the inside electrode formation portion to form the inside electrode on the inside electrode formation portion.

14. The method of claim 13, wherein in the step of relatively rotating the paste discharge hole, at the same time, the paste discharge hole is moved toward the opening of the inside space of the electrolyte member.

15. The method of claim 13, wherein in the step of relatively rotating the paste discharge hole with respect to the solid electrolyte member, one of the paste discharge hole and the solid electrolyte member rotates.

16. The method of claim 13, wherein in the step of relatively rotating the paste discharge hole with respect to the solid electrolyte member, both of the paste discharge hole and the solid electrolyte member rotate with respect to each other.

17. The method of claim 13, wherein the step of removing the nozzle includes a step of relatively moving the paste discharge hole of the nozzle with respect to the solid electrolyte member toward the opening of the inside space of the solid electrolyte member while discharging the paste to the inside surface of the solid electrolyte member.

18. The method of claim 17, wherein:
the inside electrode is composed of a reaction electrode and a lead portion;
a reaction electrode formation portion on which the reaction electrode is to be formed by the chemical plating is formed by the step of relatively rotating the paste discharge hole; and
a lead formation portion on which the lead portion is to be formed by the chemical plating is formed by the step of relatively moving the paste discharge hole toward the opening of the inside space.

19. The method of claim 18, wherein the step of relatively moving the paste discharge hole is performed after stopping rotation between the paste discharge hole and the electrolyte member.

20. The method of claim 17, wherein in the step of relatively moving the paste discharge hole toward the opening of the inside space, the paste discharge hole is relatively moved with respect to the solid electrolyte member in an axial direction of the solid electrolyte member.

21. The method of claim 17, wherein in the step of relatively moving the paste discharge hole toward the opening, one of the paste discharge hole and the solid electrolyte member is moved.

22. The method of claim 17, wherein in the step of relatively moving the paste discharge hole toward the opening, both of the paste discharge hole and the solid electrolyte member are moved.

23. The method of claim 13, further comprising a step of heating the inside electrode formation portion before the step of performing the chemical plating.

24. The method of claim 13, further comprising a step of inserting a heater into the inside space of the electrolyte member after the step of performing the chemical plating.

* * * * *